US009212336B2

(12) United States Patent
Geng et al.

(10) Patent No.: US 9,212,336 B2
(45) Date of Patent: Dec. 15, 2015

(54) 3-METHYL-BENZOFURAN-5-OL AND ITS USE IN PERFUME COMPOSITIONS

(71) Applicant: International Flavors & Fragrances Inc., New York, NY (US)

(72) Inventors: Feng Geng, Piscataway, NJ (US); Michael G. Monteleone, Hazlet, NJ (US); Anubhav P. S. Narula, Hazlet, NJ (US)

(73) Assignee: International Flavors & Fragrances Inc., New York ( * ) Notice: Subject to any disclaimer, the term of this patent is extended or adjusted under 35 U.S.C. 154(b) by 132 days.

(21) Appl. No.: 14/057,008

(22) Filed: Oct. 18, 2013

(65) Prior Publication Data

US 2015/0111810 A1    Apr. 23, 2015

(51) Int. Cl.
*C11B 9/00* (2006.01)
*A61Q 13/00* (2006.01)
*A61L 9/01* (2006.01)
*C11D 3/50* (2006.01)
*A61L 2/18* (2006.01)
*A61L 9/014* (2006.01)
*A61K 8/49* (2006.01)

(52) U.S. Cl.
CPC ............ *C11B 9/0076* (2013.01); *A61K 8/4973* (2013.01); *A61L 2/18* (2013.01); *A61L 9/01* (2013.01); *A61L 9/014* (2013.01); *A61Q 13/00* (2013.01); *C11D 3/50* (2013.01); *A61L 2202/26* (2013.01)

(58) Field of Classification Search
CPC .............................. A61Q 13/00; C11B 9/0076
USPC ........................................................... 512/13
See application file for complete search history.

(56) References Cited

U.S. PATENT DOCUMENTS

| 5,203,875 A | 4/1993 | Tuloup et al. |
| 5,730,962 A * | 3/1998 | Junino et al. .................... 424/62 |
| 2004/0231067 A1 * | 11/2004 | Cotteret et al. .................. 8/405 |
| 2011/0268802 A1 * | 11/2011 | Dihora et al. ................. 424/489 |

OTHER PUBLICATIONS

Hennings, et al., "Anion-Accelerated Palladium-Mediated Intramolecular Cyclizations: Synthesis of Benzofurans, Indoles, and a Benzopyran" Tetrahedron Letters 38(36), 1997, 6379-6382.
Youn, et al., "Facile Construction of the Benzofuran and Chromene Ring Systems via PdII-Catalyzed Oxidative Cyclization" Organic Letters 7(15), 2005, 3355-3358.

* cited by examiner

*Primary Examiner* — Ling Choi
*Assistant Examiner* — Lanee Reuther
(74) *Attorney, Agent, or Firm* — XuFan Tseng; Martin Zhang; Elizabeth M. Quirk

(57) ABSTRACT

The present invention is directed to a novel fragrance compound, 3-methyl-benzofuran-5-ol, and a method of improving, enhancing or modifying a fragrance formulation through the addition of an olfactory acceptable amount of 3-methyl-benzofuran-5-ol.

15 Claims, No Drawings

3-METHYL-BENZOFURAN-5-OL AND ITS USE IN PERFUME COMPOSITIONS

FIELD OF THE INVENTION

The present invention relates to the novel use of 3-methyl-benzofuran-5-ol as a fragrance material.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances.

SUMMARY OF THE INVENTION

The present invention provides the unexpected advantageous use of 3-methyl-benzofuran-5-ol in enhancing, improving or modifying the fragrance of perfumes, colognes, toilet waters, personal products, fabric care products, and the like.

One embodiment of the present invention is directed to 3-methyl-benzofuran-5-ol, a novel fragrance compound, represented by the following formula:

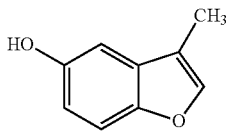

Structure I

Another embodiment of the present invention is directed to a method of improving, enhancing or modifying a fragrance formulation by incorporating an olfactory acceptable amount of 3-methyl-benzofuran-5-ol.

Another embodiment of the present invention is directed to a fragrance composition comprising 3-methyl-benzofuran-5-ol.

Another embodiment of the present invention is directed to a fragrance product comprising 3-methyl-benzofuran-5-ol.

These and other embodiments of the present invention will be apparent by reading the following specification.

DETAILED DESCRIPTION OF THE INVENTION

It has been surprisingly found that 3-methyl-benzofuran-5-ol possesses unexpected powerful and complex leathery note with natural leather feel.

3-Methyl-benzofuran-5-ol of the present invention is represented by the following structure:

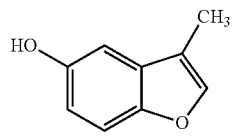

Structure I

3-Methyl-benzofuran-5-ol can be prepared according to the following reaction scheme, the details of which are specified in the Examples. The reagents were purchased from Aldrich Chemical Company unless noted otherwise.

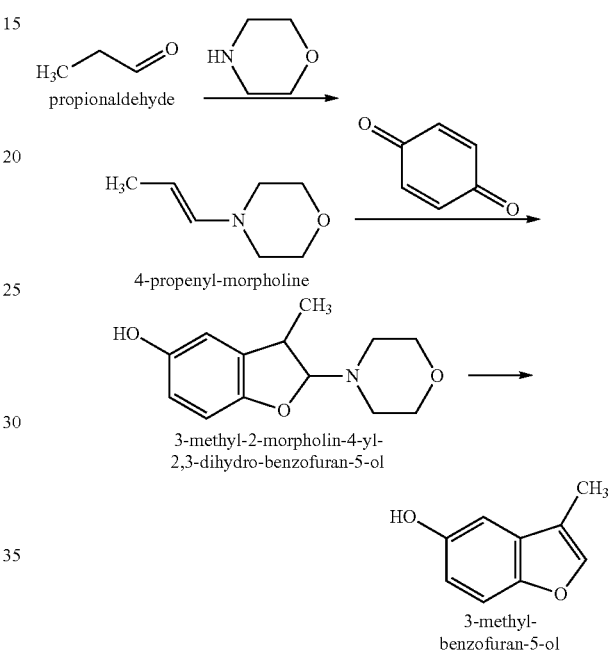

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The use of the compound of the present invention is widely applicable in current perfumery products, including the preparation of perfumes and colognes, the perfuming of personal care products such as soaps, shower gels, and hair care products, fabric care products as well as air fresheners and cosmetic preparations. This compound can also be used to perfume cleaning agents, such as, but not limited to detergents, dishwashing materials, scrubbing compositions, window cleaners and the like. In these preparations, the compound of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry;

musk; and flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compound of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), 2-ethyl-4-(2,2,3-trimethyl-3-cyclopenten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising the compound of the present invention. The fragrance formulation of the present invention may comprise the compound of the present invention and further a complementary fragrance compound as defined above.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains the compound of the present invention. The fragrance product of the present invention may contain the compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

Olfactory acceptable amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica.

When used in a fragrance formulation this ingredient provides powerful and complex leathery note with natural leather feel that make the fragrance formulation more desirable and noticeable and add the perception of value. All of the odor qualities found in this material assist in beautifying and enhancing the finished accord improving the performance of the other materials in the fragrance.

The following are provided as specific embodiments of the present invention. Other modifications of this invention will be readily apparent to those skilled in the art. Such modifications are understood to be within the scope of this invention. The chemical materials used in the preparation of the compounds of the present invention are commercially available from Aldrich Chemical Company. As used herein all percentages are weight percent unless otherwise noted, ppm is understood to stand for parts per million, mol is understood to be mole, L is understood to be liter, mL is understood to be milliliter, Kg is understood to be kilogram, g is understood to be gram, and psi is understood to be pound-force per square inch. IFF as used in the examples is understood to mean International Flavors & Fragrances Inc., New York, N.Y., USA.

Example I

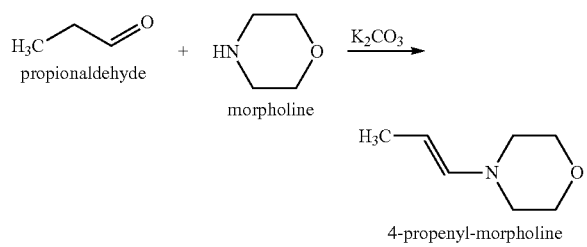

Preparation of 4-Propenyl-morpholine

A reaction flask was charged with morpholine (938 g, 10.8 mol) and potassium carbonate ($K_2CO_3$) (800 g, 5.8 mol) and heated to 40° C. with stirring. Propionaldehyde (500 g, 8.6 mol) was added dropwise while the temperature was kept under 60° C. with a water bath. After the completion of the addition, the reaction mixture was aged for two hours and filtered. The obtained filtrate was further distilled to provide 4-propenyl-morpholine (850 g, 6.7 mol).

$^1$H NMR (CDCl$_3$, 500 MHz): 5.79 ppm (d, 1H, J=5.79 ppm), 4.43 ppm (dd, 1H, J$_1$=13.95 Hz, J$_2$=6.55 Hz), 3.69 ppm (t, 4H, J=4.86 Hz), 2.78 ppm (t, 4H, J=4.86 ppm), 1.62 ppm (d, 3H, J=6.25 Hz)

Example II

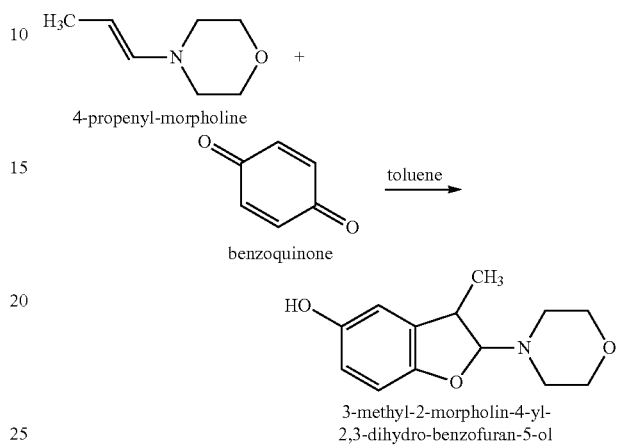

Preparation of 3-Methyl-2-morpholin-4-yl-2,3-dihydro-benzofuran-5-ol

Benzoquinone (300 g, 2.8 mol) was added in toluene (1.5 L) and cooled with a dry ice/isopropyl alcohol (IPA) bath. 4-Propenyl-morpholine (prepared as above in EXAMPLE I) (380 g, 3 mol) was added dropwise with stirring. The reaction mixture was aged for overnight, filtered and subsequently air dried to provide 3-methyl-2-morpholin-4-yl-2,3-dihydro-benzofuran-5-ol (628 g, 2.7 mol).

$^1$H NMR (CDCl$_3$, 400 MHz): 6.59 ppm (m, 3H), 6.15 ppm-5.28 ppm (bs, 1H), 4.90 ppm (d, 1H, J=5.05 Hz), 3.71 ppm (t, 4H, J=4.71 Hz), 3.27 ppm (m, 1H), 2.89 ppm (m, 2H), 2.66 ppm (m, 2H), 1.31 ppm (d, 3H, J=7 Hz)

Example III

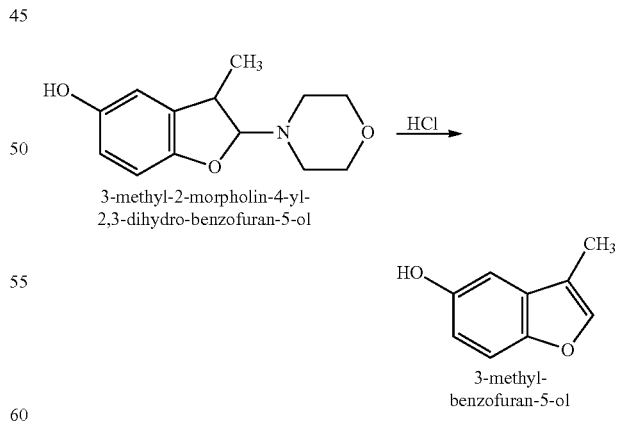

Preparation of 3-Methyl-benzofuran-5-ol (Structure I)

3-Methyl-2-morpholin-4-yl-2,3-dihydro-benzofuran-5-ol (prepared as above in EXAMPLE II) (628 g, 2.7 mol) was added to hydrochloric acid (HCl) (20%, 2 L) at room temperature with stirring. The reaction mixture was heated to 56° C. for 3 hours and then cooled down. The crude was extracted with toluene (500 mL) for three times. The organic phases were obtained, combined and evaporated to provide a crude product, which was further recrystallization to afford 3-methyl-benzofuran-5-ol (290 g, 2 mol).

$^1$H NMR (CDCl$_3$, 400 MHz): 7.37 ppm (s, 1H), 7.29 ppm (d, 1H, J=8.87 Hz), 6.92 ppm (d, 1H, J=2.37 Hz), 6.79 ppm (dd, 1H, J$_1$=8.87 Hz, J$_2$=2.37 Hz), 4.622 ppm (bs, 1H), 2.18 ppm (s, 3H)

Example IV

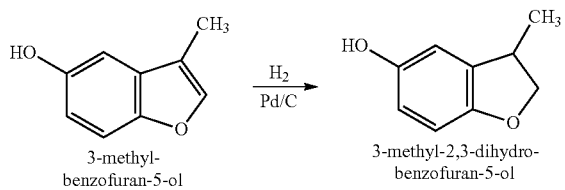

Preparation of 3-Methyl-2,3-dihydro-benzofuran-5-ol (Structure II)

3-Methyl-benzofuran-5-ol (prepared as above in EXAMPLE III) (245 g, 1.6 mol) was added in tetrahydrofuran (THF) (450 mL) and hydrogenated with palladium on carbon (Pd/C) (5%, 2.4 g) under hydrogen (H$_2$) (200 psi) at 145° C. for about 8 hours till gas chromatograph (GC) analysis showed completion of the reaction. The obtained mixture was filtered and distilled to afford 3-methyl-2,3-dihydro-benzofuran-5-ol (190 g, 1.3 mol).

$^1$H NMR (CDCl$_3$, 500 MHz): 6.6 ppm (d, 1H, J=2.65 Hz), 6.62 ppm (d, 1H, J=8.67 Hz), 6.57 ppm (dd, 1H, J$_1$=8.67 Hz, J$_2$=2.67 Hz), 5.93 ppm (bs, 1H), 4.64 ppm (t, 1H, J=8.77 Hz), 4.03 ppm (t, 1H, J-8.77 Hz) 3.45 ppm (m, 1H) 1.25 ppm (d, 3H, J=6.77 ppm)

Example V

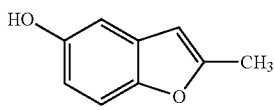

Preparation of 2-Methyl-benzofuran-5-ol (Structure III)

2-Methyl-benzofuran-5-ol was prepared as described in Hennings, et al., Tetrahedron Letters 38(36): 6379-6382 (1997).

$^1$H NMR (CDCl$_3$, 400 MHz): 7.94 ppm (bs, 1H), 7.02 ppm (d, 1H, J=8.8 Hz), 6.90 ppm (s, 1H), 6.72 ppm (d, 1H, J=8.8 Hz), 6.30 ppm (s, 1H), 2.38 ppm (s, 3H)

Example VI

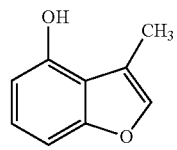

Preparation of 3-Methyl-benzofuran-4-ol (Structure IV)

3-Methyl-benzofuran-4-ol was prepared as described in Youn, et al., Organic Letters 7(15): 3355-3358 (2005).

$^1$H NMR (CDCl$_3$, 400 MHz): 7.26 ppm (m, 1H), 7.01-7.09 ppm (m, 2H), 6.51 ppm (dd, 1H, J$_1$=2.54 Hz, J$_2$=1.25 Hz), 5.08 ppm (bs, 1H), 2.39 ppm (s, 3H)

Example VII

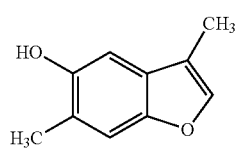

Structure V

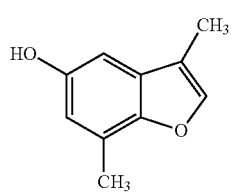

Structure VI

Preparation of 3,6-Dimethyl-benzofuran-5-ol (Structure V) and 3,7-Dimethyl-benzofuran-5-ol (Structure VI)

3,6-Dimethyl-benzofuran-5-ol and 3,7-dimethyl-benzofuran-5-ol were similarly prepared according to EXAMPLEs I-III while 2-methyl-benzoquinone was used to replace benzoquinone in EXAMPLE II. The final products of 3,6-dimethyl-benzofuran-5-ol and 3,7-dimethyl-benzofuran-5-ol were separated using silica gel chromatography.

3,6-Dimethyl-benzofuran-5-ol (Structure V) has the following NMR spectral characteristics:

$^1$H NMR (CDCl$_3$, 500 MHz): 7.30 ppm (s, 1H), 7.20 ppm (s, 1H), 6.87 ppm (s, 1H), 4.59 ppm (bs, 1H), 2.35 ppm (s, 3H), 2.17 ppm (s, 3H)

3,7-Dimethyl-benzofuran-5-ol (Structure VI) has the following NMR spectral characteristics:

$^1$H NMR (CDCl$_3$, 500 MHz): 7.37 ppm (s, 1H), 6.74 ppm (d, 1H, J=2.54 Hz), 6.62 ppm (d, 1H, J=2.54 Hz), 4.57 ppm (bs, 1H), 2.45 ppm (s, 3H), 2.17 ppm (s, 3H)

Example VIII

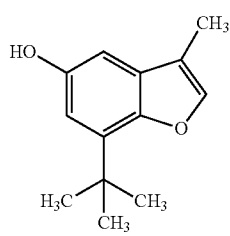

Preparation of
7-tert-Butyl-3-methyl-benzofuran-5-ol (Structure VII)

7-tert-Butyl-3-methyl-benzofuran-5-ol was similarly prepared according to EXAMPLEs I-III. 2-tert-Butyl-benzoquinone was used to replace benzoquinone in EXAMPLE II.

$^1$H NMR (CDCl$_3$, 500 MHz): 7.36 ppm (s, 1H), 6.76 ppm (d, 1H, J=2.61 Hz), 6.73 ppm (d, 1H, J=2.61 Hz), 5.41 ppm (bs, 1H), 2.13 ppm (s, 3H), 1.43 ppm (s, 9H)

Example IX

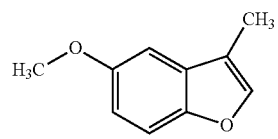

Preparation of 5-Methoxy-3-methyl-benzofuran (Structure VIII)

5-Methoxy-3-methyl-benzofuran was prepared via methylation of 3-methyl-benzofuran-5-ol (Structure I) (prepared as above in EXAMPLEs I-III) using methyl iodide (MeI).

$^1$H NMR (CDCl$_3$, 400 MHz): 7.37 ppm (s, 1H), 7.33 ppm (d, 1H, J=8.96 Hz), 66.96 ppm (s, 1H), 6.88 ppm (d, 1H, J=8.96 Hz), 3.858 ppm (s, 3H), 2.21 ppm (s, 3H)

Example X

The fragrance properties of the above compounds (i.e., Structures I-VIII) were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Chemical Name | Compound | Odor Profile | Strength | Complexity |
| --- | --- | --- | --- | --- |
| 3-Methyl-benzofuran-5-ol (Structure I) | | Very powerful and complex leathery note with natural leather feel. Further animalic, earthy and slightly phenolic notes provided body, complexity and uniqueness. Additional slightly anisic, balsamic, vanillic and powdery notes added creaminess. | 9 | 9 |
| 3-Methyl-2,3-dihydro-benzofuran-5-ol (Structure II) | | Leathery note but less powerful or complex with a thinner body. | 5 | 5 |
| 2-Methyl-benzofuran-5-ol (Structure III) | | Balsamic, sweet and earthy notes supported by mossyness character with slightly leathery aspect. Appeared to be in an odor region distinct from that of Structure I. | 6 | 5 |
| 3-Methyl-benzofuran-4-ol (Structure IV) | | Balsamic, sweet and less animalic notes with more phenolic character and chemical quality. | 5 | 5 |

| Chemical Name | Compound | Odor Profile | Strength | Complexity |
|---|---|---|---|---|
| 3,6-Dimethyl-benzofuran-5-ol (Structure V) | | Leathery note but less powerful or complex with more green and animalic characters and crude quality. | 5 | 5 |
| 3,7-dimethyl-benzofuran-5-ol (Structure VI) | | Weak with bacon and fatty characters. | 2 | 2 |
| 7-tert-Butyl-3-methyl benzofuran-5-ol (Structure VII) | | Weak and chemical with a thin body and kerosene like and green characters. | 2 | 2 |
| 5-Methoxy-3-methyl-benzofuran (Structure VIII) | | Leathery note but less powerful or complex with chemical and kerosene-like quality. Less animalic and phenolic with balsamic character. | 4 | 3 |

Example X

Continued

Structure I exhibited particularly desirable, strong, and complex odors, superior to Structures II-VIII. Its advantageous properties are unexpected.

What is claimed is:

1. A method of improving, enhancing or modifying a fragrance formulation through the addition of an olfactory acceptable amount of 3-methyl-benzo furan-5-ol.

2. The method of claim 1, wherein the olfactory acceptable amount is from about 0.005 to about 50 weight percent of the fragrance formulation.

3. The method of claim 1, wherein the olfactory acceptable amount is from about 0.5 to about 25 weight percent of the fragrance formulation.

4. The method of claim 1, wherein the olfactory acceptable amount is from about 1 to about 10 weight percent of the fragrance formulation.

5. A fragrance formulation containing an olfactory acceptable amount of 3-methyl-benzofuran-5-ol.

6. The fragrance formulation of claim 5, wherein the olfactory acceptable amount is from about 0.005 to about 50 weight percent of the fragrance formulation.

7. The fragrance formulation of claim 5, wherein the olfactory acceptable amount is from about 0.5 to about 25 weight percent of the fragrance formulation.

8. The fragrance formulation of claim 5, wherein the olfactory acceptable amount is from about 1 to about 10 weight percent of the fragrance formulation.

9. The fragrance formulation of claim 5 further comprising a material selected from the group consisting of a polymer and a non-polymer.

10. The fragrance formulation of claim 9, wherein the non-polymer is selected from the group consisting of an oligomer, a surfactant, an emulsifier, a fat, a wax, a phospholipid, an organic oil, a mineral oil, a petrolatum, a natural oil, a perfume fixative, a fiber, a starch, a sugar and a solid surface material.

11. The fragrance formulation of claim 10, wherein the solid surface material is selected from the group consisting of zeolite and silica.

12. A fragrance product containing an olfactory acceptable amount of 3-methyl-benzofuran-5-ol.

13. The fragrance product of claim 12, wherein the fragrance product is selected from the group consisting of a perfume, a cologne, toilet water, a cosmetic product, a personal care product, a fabric care product, a cleaning product and an air freshener, a bar soap, a liquid soap, a shower gel, a foam bath, a cosmetic, a skin care product, a hair care product, a deodorant, an antiperspirant, a feminine care product, a baby care product, a family care product, a fabric product, an air care product, a fragrance delivery system, a cosmetic preparation, a cleaning agent, a disinfectant, a washing agent, a dental and oral hygiene product, a health care and nutritional product and a food product.

14. The fragrance product of claim 13, wherein the cleaning product is selected from the group consisting of a detergent, a dishwashing material, a scrubbing composition, a glass cleaner, a metal cleaner, a countertop cleaner, a floor cleaner, a carpet cleaner, a toilet cleaner and a bleach additive.

15. The fragrance product of claim 13, wherein the washing agent is selected from the group consisting of a laundry detergent and a rinse additive.

\* \* \* \* \*